United States Patent [19]
Chang

[11] Patent Number: 5,981,272
[45] Date of Patent: Nov. 9, 1999

[54] COMPOSITE MEDIUM FOR ATTACHING AND GROWING MICROORGANISMS

[76] Inventor: Huai Ted Chang, 557 Dover Ct., Buffalo Grove, Ill. 60089-6698

[21] Appl. No.: 08/413,593

[22] Filed: Mar. 30, 1995

[51] Int. Cl.⁶ .............................. C12M 1/14; C12M 3/04; C12N 11/08; C02F 3/00
[52] U.S. Cl. .................. 435/299.1; 435/176; 435/180; 435/186; 210/615; 210/616; 210/617; 210/150
[58] Field of Search .................. 502/413, 7, 416; 210/615, 616, 617, 150; 427/186; 435/176, 180, 299.1; 71/64.07

[56] References Cited

U.S. PATENT DOCUMENTS

| | | | |
|---|---|---|---|
| 3,093,462 | 6/1963 | Rapaport | 434/84 |
| 3,315,374 | 4/1967 | Geraty | 434/84 |
| 4,556,595 | 12/1985 | Ochi | 428/143 |
| 5,037,791 | 8/1991 | Comolli et al. | 502/185 |
| 5,167,989 | 12/1992 | Dudek et al. | 427/202 |
| 5,580,770 | 12/1996 | DeFilippi | 435/180 |

*Primary Examiner*—Marian C. Knode
*Assistant Examiner*—In Suk Bullock
*Attorney, Agent, or Firm*—Charles F. Lind

[57] ABSTRACT

A new composite material for process application is described in this document. The composite material combine a regular base material (10) and small particles (14) using a layer of adhesive (12). The base material can be a sheet (10), a molded packing ring medium (16), or a structured packing medium. The material made of the base material can be plastics, ceramics, metals, porous materials, adsorptive materials, etc. The particles can be activated carbons, charcoals, anthracites, sands, and glass beads. The bound particles increase the surface roughness and the surface area of the base material by providing valleys (20) and crevices (22).

8 Claims, 1 Drawing Sheet

COMPOSITE MEDIUM FOR ATTACHING AND GROWING MICROORGANISMS

BACKGROUND

1. Field of Invention

This invention is a composite material which uses adhesive to bind particles to a manufactured medium. The composite medium can be used to fill (i.e., pack) reactors for biological waste treatment in pollution control process. The reactors can be used to treat gaseous and liquid waste streams.

BACKGROUND

2. Description of Prior Art

In pollution control technology, one of the effective biological reactors involves using microorganisms attached to a surface to remove pollutants. These types of the reactors are called attached-growth processes, biofilm processes, or immobilized-cell processes.

Originally these biofilm reactors used rocks to pack the reactors. Microorganisms were grown on the surface of the rocks. Waste streams were passed through the reactors. Organic and inorganic pollutants came into contact with the microorganisms and were removed. The disadvantages of using the rocks as the packing media include the following:

(a) Rocks are very heavy and difficult to handle.

(b) The reactors require high structural strength to contain the rocks.

(c) The support for the media requires high structural strength to sustain the pressure of the rocks.

Later, plastic media were used to replace rocks as the packing material for the biofilm processes. The plastic media offered several advantages over the rocks.

(a) Plastic media are light-weight and easier to handle.

(b) Plastic media can be manufactured into different shape and size.

(c) Plastic media can be manufactured into a form with high surface area per unit volume of the packing media.

(d) Various plastic materials can be used to manufacture the packing media. For example, polypropylene, polyethylene, polyvinyl chloride (PVC), and Teflon® (PTFE) have been used.

However, the surface of the plastic media were very smooth due to the extrusion and molding processes. The smooth surface were not suitable for microorganisms to attach to the plastic media. The disadvantages of the smooth surface include the following.

(a) High rate of microorganisms loss due to fluid dynamic pressure.

(b) Low rate of microorganisms attachment due to the smooth surface.

These disadvantages resulted in long startup time and low treatment efficiency for the biofilm processes.

Later technology used particulate materials as the packing media for the biofilm processes. Examples for these particulate materials include sands, anthracites, and granular activated carbons (GAC). The particles provide a large amount of rough surface area for microorganisms attachment and growth. This alleviated the problems associated with the smooth surface of the plastic media. However, packing particles in a reactor introduced other problems as described below.

(a) The voids between packed particles cannot be controlled.

(b) The voids between packed particles are small. This resulted in high pressure drop for waste streams to flow through the reactor.

(c) As microorganisms grow and increase in amount during process operation, the voids are filled with the microorganisms and became smaller. This phenomenon resulted in increased pressure drop and eventually clogging of the reactor. The reactor must be taken out of service and back-washed or mechanically agitated to remove the excess microorganisms. The downtime is time lost and the back-washing equipment complicates reactor design, construction, and operation.

OBJECTS AND ADVANTAGES

Accordingly, several objects and advantages of the present invention are:

(a) to provide a packing medium which allows microorganisms to attach easily and efficiently;

(b) to provide a packing medium which protects microorganisms from fluid shear forces;

(c) to provide a packing medium which minimizes the disruption to biological growth;

(d) to provide a packing medium which shortens the startup time of the biological processes using the medium;

(e) to provide a packing medium which increases the efficiency of the biological processes using the medium;

(f) to provide a packing medium which holds the moisture for biological growth. This advantage is essential in the treatment of vapor phase wastes.

Further objects and advantages are to provide a packing medium which can be handled and packed in a reactor easily, and which can be manufactured easily and inexpensively. Still further objects and advantages will become apparent from a consideration of the ensuing description and drawings.

DRAWING FIGURES

In the drawings, closely related figures have the same number but different alphabetic suffixes.

REFERENCE NUMERALS IN DRAWINGS

| Number | Explanation |
| --- | --- |
| 10 | sheet base material |
| 12 | adhesive |
| 14 | particles |
| 16 | ballast ® ring base material |
| 18 | spoke |
| 20 | valley |
| 22 | crevice |

Figure 1:
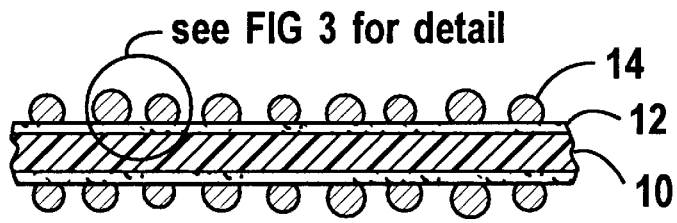
FIG. 1 shows the composite medium made of particles bound to a flat surface (e.g., plastic sheet).
Figures 2A, 2B:
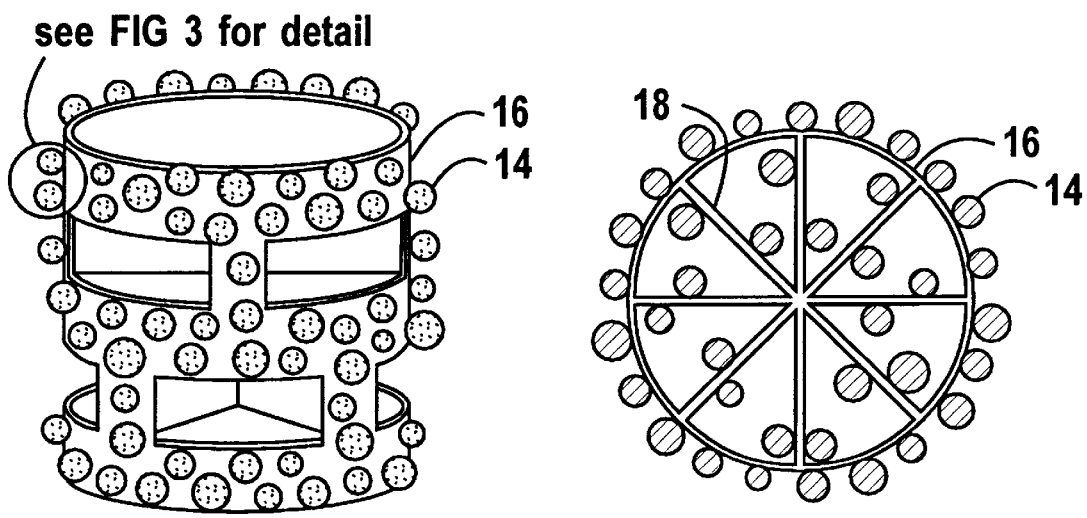
FIGS. 2a and 2b show the composite medium made of particles bound to a ballast® ring (Century Plastics, Inc.).
Figure 3:
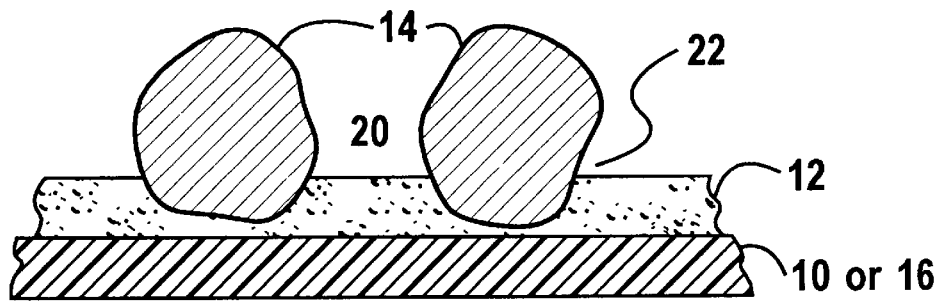
FIG. 3 shows the details of the composite medium surface.

DESCRIPTION—FIGS. 1 to 3

FIG. 1 shows a typical configuration of a packing medium coated with particles (Item 14). The medium in the figure is a flat sheet (Item 10) which may be made of plastics or other materials.

The medium is first coated with a thin layer of adhesive (Item 12) as an epoxide resin. The adhesive can be applied by brushing or spraying. Before the adhesive is dried and hardened, the particles are sprinkled onto the surface of the medium. Part of the particles will be immersed in the layer of the adhesive. After the adhesive is hardened, the manufacturing of the composite medium is completed. The flat sheet composite medium can be applied in the horizontal position, vertical positions, and other positions.

FIG. 2 shows the configuration of a ballast® ring packing medium (Item 16) coated with particles. FIG. 2a shows the side-view of the ring and FIG. 2b shows the top-view of the ring. The coating procedure is the same as the flat sheet. The composite packing medium can be used just like the regular ballast® ring. It can be packed in a trickling filter, in a packed bed biological process, in a biofilter for treating gaseous wastes, and in an air stripper.

FIG. 3 shows the details of the particles coated on a base material surface. The particles are partially embedded in the adhesive and create valleys (Item 20) and crevices or niches (Item 22).

From the description above, a number of advantages of my composite media become evident:

(a) The surface roughness and surface area of the regular media are increased significantly. The particles create valleys and provide enormous niches.

(b) The valleys and niches protect microorganisms from fluid shear forces, minimize the disruption to biological growth, and allow microorganisms to attach easily and efficiently.

(c) As a result of the above advantages, the process using the composite media will have a shorter startup time and a higher treatment efficiency.

(d) The valleys and niches hold moisture in the treatment of vapor phase wastes. The moisture is essential to biological growth in the treatment of organic contaminants in gaseous wastes.

OPERATION—FIGS. 1 to 3

To use the composite media, the media are placed or packed in a vessel (i.e., reactor). For flat sheet composite media, a series of sheets can be placed on a shaft with a spacer separating two sheets. The entire assembly can be placed in the reactor. The wastewater to be treated is passed from one end (called inflow or influent) of the reactor and flow through the composite media where degradation occurs. The treated (i.e., clean) wastewater is discharged from the other end (called outflow or effluent) of the reactor.

For composite packing media, the media can be packed in a vessel (i.e., reactor). The wastewater is introduced from the inflow end of the reactor. The wastewater is treated as it flows pass the composite media. The treated wastewater is discharged from the outflow end of the reactor.

Summary, Ramifications, and Scope

Accordingly, the composite media of this invention can be used to grow microorganisms: (1) to convert contaminants in liquid wastewater to benign products in pollution control; (2) to convert chemicals (reactants) to products in chemical processing; (3) to convert chemicals (reactants) to products in food processing; (4) to convert chemicals (reactants) to products in pharmaceutical processing; (5) to convert contaminants in vapor phase to benign products in pollution control.

Furthermore, the composite media have the additional advantages in that:

(1) It provides an easy and inexpensive manufacturing process.

(2) When porous particles are used as the coating material, the particles individually will provide enormous secondary pores in addition to the valleys and niches on the particles collectively, suited for biological growth.

(3) When particles with adsorptive capabilities are used as the coating material, the particles can adsorb and remove (undesirable) compounds from the process streams (liquid and gas).

(4) The porous and adsorptive particles can reduce the startup time and increase the treatment efficiency.

(5) Porous and adsorptive material can be used as the base or substate for bounding particles to provide additional pores and crevices, and adsorptive capacities.

(6) Porous and adsorptive adhesive can be used to provide additional pores and crevices, and adsorptive capacities.

Although the description above contains many specificities, these should not be construed as limiting the scope of the invention but as merely providing illustrations of some of the presently preferred embodiments of this invention. For example, the composite media can use different shape materials (e.g., sheet, molded packing, structured packing) as the base or substrate for coating particles; the base material can be made of different material such as plastics, ceramics, metals, porous materials, adsorptive materials, etc.; the particles can be any small diameter particles such as activated carbons, charcoals, anthracites, sands, and glass beads.

Thus the scope of the invention should be determined by the appended claims and their legal equivalents, rather than by the examples above.

References

Wastewater Engineering-Treatment, Disposal, and Reuse, Third edition, Metcalf and Eddy, Revised by G. Tchobanoglous and F. L. Burton, McGraw-Hill, Inc, New York, 1991.

Young, J. C and Young, H. W, "Full-Scale Treatment of Chemical Process Wastes Using Anaerobic Filters," *Research Journal Water Pollution Control Federation*, Vol. 63, No. 2, pp. 153–159, 1991.

Kindzierski, W. B., Gray, M. R., Fedorak, P. M., and Hrudey, S. E., "Activated Carbon and Synthetic Resins as Support Material for Methanogenic Phenol-Degrading Consortia-Comparison of Surface Characteristics and Initial Colonization," *Water Environment Research*, Vol. 64, No. 6, pp. 766–775, 1992.

Product Catalog, Century Plastics, Inc., P.O. Box 789, El Dorado, Kans. 67042. Tel: 316-321-1153.

I claim:

1. A composite packing medium for attaching and growing microorganisms thereon, comprising the combination of
   a substantially rigid substrate having a surface; and
   a plurality of randomly shaped particles randomly secured by an adhesive coating onto and substantially over said substrate surface and protruding beyond the adhesive coating and defining overall an irregular rough exterior layer extended along the substrate surface, and the adjacent particles further forming therebetween a plurality of irregularly shaped recessed valleys and crevices, the exposed protruding particles having the microorganisms become attached thereto and therebetween.

2. A composite packing medium according to claim 1, wherein said substrate is selected from the group consisting of plastic, ceramic, metals or wood.

3. A composite packing medium according to claim 1, wherein said particles are selected from the group consisting of activated carbon, charcoal, anthracites, sands, and glass beads.

4. A composite packing medium according to claim 1, wherein said substrate is in the form of a flat sheet, a ballast ring or honeycomb.

5. A composite packing medium according to claim 1, wherein said substrate is selected from the group consisting of plastic, ceramic, metals or wood; and wherein said particles are selected from the group consisting of activated carbon, charcoal, anthracites, sands, and glass beads.

6. A composite packing medium according to claim 1, wherein said substrate is a plastic, having said exterior surface substantially smooth and impervious; and wherein said particles are activated carbons or charcoal, being porous and adsorptive.

7. A composite packing medium according to claim 1, wherein said substrate is in the form of a flat sheet.

8. A composite packing medium according to claim 1, wherein said substrate is in the form of a ballast ring or honeycomb.

\* \* \* \* \*